United States Patent [19]

Donohue

[11] Patent Number: 4,582,925

[45] Date of Patent: Apr. 15, 1986

[54] TETRAMETHYLBIPHENYLCARBOXYLIC ACIDS AND DERIVATIVES THEREOF

[75] Inventor: John A. Donohue, Elmhurst, Ill.

[73] Assignee: Standard Oil Company (Indiana), Chicago, Ill.

[21] Appl. No.: 263,900

[22] Filed: May 15, 1981

Related U.S. Application Data

[60] Division of Ser. No. 60,907, Jul. 26, 1979, abandoned, which is a continuation of Ser. No. 622,649, Oct. 15, 1975, abandoned, which is a continuation-in-part of Ser. No. 515,506, Oct. 24, 1974, abandoned.

[51] Int. Cl.$^4$ .................... C07C 63/72; C07C 69/76
[52] U.S. Cl. .................... 560/76; 562/488; 562/412; 260/544 P; 528/65; 528/66; 528/85; 528/308; 528/347; 528/348
[58] Field of Search .................... 260/544 P; 562/488; 560/76

[56] References Cited

U.S. PATENT DOCUMENTS 3,876,691  4/1975  Lincoln .......................... 562/484

OTHER PUBLICATIONS

Nomura, Yujiro et al., *J. Chem. Soc.,* (B) (1970) pp. 956–960.
Wagner et al., "Synthetic Organic Chemistry" (1965) pp. 412–415, John Wiley & Sons, Publ.

*Primary Examiner*—Natalie Trousof
*Assistant Examiner*—L. Hendriksen
*Attorney, Agent, or Firm*—William H. Magidson; William T. McClain; Ralph C. Medhurst

[57] ABSTRACT

2,2',6,6'-Tetramethyl-4,4'-dicarboxylic acid is prepared by the oxidation of bimesityl and derivatives of the dicarboxylic acid are used in the preparation of polyesters of high molecular weight.

7 Claims, No Drawings

TETRAMETHYLBIPHENYLCARBOXYLIC ACIDS AND DERIVATIVES THEREOF

This is a division of application Ser. No. 060,907 filed July 26, 1979, which is a continuation of U.S. Ser. No. 622,649 filed Oct. 15, 1975, which is a continuation-in-part of U.S. Ser. No. 517,506 filed Oct. 24, 1974 all now abandoned.

This invention relates to 2,2',6,6'-tetramethylbiphenyl-4,4'-dicarboxylic acid compounds suitable for producing polymers useful for forming shaped objects, such as film, fiber and molded parts.

As is well known, the mechanical and physical properties of a fiber or film depends on the chemical structure of the polymer from which it is made. For example, the melting point and glass transition temperature of a polymer composition controls many of the physical properties of shaped objects. The melting point determines thermal resistance, safe ironing temperature and heat-setting temperature of fibers. Glass transition temperature (Tg) determines initial modulus, tensile strain recovery, work of recovery, drape and hand, wash-and-wear characteristics, comfort factors and resilience of fibers. The main molecular factors which influence these properties include chain stiffness, the intermolecular forces, orientation and crystallinity.

Accordingly, there has been considerable interest in developing aromatic symmetrical acids as precursors for thermally stable polymers, such as polyesters or polyamides. It is well known that the introduction of aromatic units in the polymer chain backbone results in high bond energies, a low degree of reactivity, and rigidity of the polymer chain structure. The use of aliphatic units in the polymer chain backbone results in flexibility, lower temperature characteristics and decreased strength as compared with the aromatic types.

Substantially all commercial polyester fibers are based on terephthalic acid. While these fibers have many excellent properties there is a need for polyester fibers having a higher Tg than provided by terephthalic acid polyesters. Recently, 2,6-naphthalene dicarboxylic acid has been proposed as a suitable aromatic acid for producing polyesters suitable for the tire cord. This acid provides polyesters having a higher Tg than those based on terephthalic acid. For example, poly(ethylene terephthalate) has a Tg of about 75° C. while poly(ethylene 2,6-naphthalene dicarboxylate) has a Tg of about 115°–125° C. However, the difficulties of manufacturing the precursor, i.e., 2,6-dimethylnaphthalene, has made the production of this acid technically difficult and economically costly. The acid requires a four-step synthesis with attendant loss in yield and consequently high cost.

Various other organic polymers have been suggested for use as high temperature fibers, such as copolyamides (Kevlar), polybenzimidazoles, polyoxadiazoles, polyimides and phenylene ring systems (polyphenylenes). Polyarylates and polycarbonates have been suggested for use as engineering plastics. However, all of these are costly and/or difficult to manufacture. Accordingly, there is a need for new aromatic acids suitable for preparing polymers for many uses.

The general object of this invention is to provide a new aromatic polycarboxylic acid compound and polymers thereof. A more specific object of this invention is to provide a new polycarboxylic acid, specifically 2,2',6,6'-tetramethylbiphenyl-4,4'-dicarboxylic acid and a method for its production. A further object is to provide novel poymers, both polyamides and polyesters, made from these acids and their simple esters. Other objects appear hereinafter.

In one aspect this invention relates to tetramethylbiphenyl dicarboxylic acid compounds (acids and esters of monohydroxy compounds).

In a second aspect this invention relates to a method of producing tetramethylbiphenyl dicarboxylic acid compounds.

In a third aspect this invention relates to polyesters based on tetramethylbiphenyl dicarboxylic acid compounds.

In a fourth aspect this invention relates to polyamides based on tetramethylbiphenyl dicarboxylic acid compounds.

These compounds (acids, acyl halides, simple esters, e.g., methyl, etc.) are desirable intermediates for producing condensation polymers, such as polyamides and polyesters suitable for forming shaped articles such as film, fiber and molded parts. The esters of this acid and monohydroxy compounds containing 4 to 24 carbon atoms can be used as plasticizers for polyvinylchloride (PVC).

Although an abstract of an article by Y. Nomura and Y. Takeuchi (*J. Chem. Soc.* (B) 1970, 956–960) mentions the structure 2,2',6,6'-tetramethylbiphenyl-4,4'-dicarboxylic acid and its methyl ester, there is no further reference to these compounds or to their properties or preparation given in the abstract or in the article. There is no indication that these compounds were made nor suggestion how to make these compounds. Low yields of other substituted biphenyls are reported by the authors. For example, 4.8 grams of 4,4'-diamino-2,2',6,6'-tetramethylbiphenyl was prepared in 52% yield from 3,5-dimethylnitrobenzene which in turn yielded only 0.10 grams of 4,4'-dicyano-2,2',6,6'-tetramethylbiphenyl in 2% yield, and an overall yield of only 1% to the dicyano compound.

I have now found that 2,2',6,6'-tetramethylbiphenyl-4,4'-dicarboxylic acid can be prepared by the oxidation of the para methyl groups of bimesityl using molecular oxygen in the presence of a cobalt compound, as for example cobaltic acetate; and the process is especially convenient and advantageous if carried out in the presence of an organic acid, preferably acetic acid. The ortho-methyl groups (the 2 and 6 methyl substituents of the bimesityl) are relatively stable and the oxidation yields primarily 2,2',6,6'-tetramethylbiphenyl-4,4'-dicarboxylic acid or its precursor which can be oxidized to the diacid.

In somewhat greater detail bimesityl is reacted with an oxygen-containing gas (oxygen, air, etc.) in the presence of cobaltic ions at a temperature within the range of 20° to 150° C., preferably 70° to 120° C., under pressure. While the reaction can be carried out neat, it is generally preferred to use an organic solvent to prevent sublimation of the bimesityl. Suitable organic carboxylic acids include acetic acid, propionic acid, benzoic acid, etc. Approximately 0.01 to 3 parts by weight cobaltic ion per part by weight bimesityl compound can be used. In general the higher the concentration of cobaltic ion the faster the rate of oxidation. The acid can be isolated by conventional means or esterified with a lower alcohol (methanol, ethanol, isopropanol) to facilitate separation and purification.

2,2',6,6'-tetramethylbiphenyl-4,4'-dicarboxylates can be produced by reacting the appropriate 2,2',6,6'-tetramethylbiphenyl-4,4'-dicarboxylic acid compound (free acid or acyl halide) with a suitable monohydroxy compound at a temperature of 60° to 200° C. or the dimethyl ester can be produced first and the appropriate diester produced by transesterification with a suitable monohydroxy compound at a temperature of 60° to 200° C.

Suitable monohydroxy compounds useful for producing these monohydroxy esters include alcohols containing from 1 to 24 carbon atoms such as methyl alcohol, ethyl alcohol, isopropyl alcohol, allyl alcohol, methallyl alcohol, n-butyl alcohol, n-hexyl alcohol, n-octyl alcohol, 2-ethylhexyl alcohol, decyl alcohol, tridecyl alcohol, stearyl alcohol, oleyl alcohol, tetracosyl alcohol; aromatic hydroxy compounds containing from 6 to 24 carbon atoms, such as phenol, cresol, para-stearylphenol, naphthol, etc., benzyl alcohol, etc.

These esters can be produced under conventional reaction conditions by reacting from about 1 to 10 moles of monohydroxy compound per carboxyl equivalent of said tetramethylbiphenyl dicarboxylic acid compound to form a solution of ester and monohydroxy compound. If desired esterification catalysts or transesterification catalysts can be used, such as sulfuric acid, phosphoric acid, para toluene sulfonic acid, benzene sulfonic acid, stannous octoate, boron trifluoride etherate, tetralkyl titanates and zirconates of U.S. Pat. No. 3,056,818, etc.

The esters of monohydroxy compounds containing from 1 to 4 carbon atoms in each alkyl group can be used advantageously in ester interchange processes for producing high molecular weight polyesters while the diesters containing from 1 to 24 carbon atoms in each ester moiety, preferably alkyl groups containing from about 4 to 13 carbon atoms, can be used as plasticizers for resinous polymers of vinyl chloride containing at least 50 mole percent vinyl chloride units. The resinous polymers of vinyl chloride include homopolymeric polyvinyl chloride, 95/5 vinyl chloride/vinyl acetate copolymers, etc. The plasticizers can be used in a concentration of from 5 to 300 parts by weight per each 100 parts by weight resinous polymer of vinyl chloride as the sole plasticizer or together with other plasticizers such as dioctyl phthalate, trioctyl phosphate, epoxidized glyceride oils, etc.

The 2,2',6,6'-tetramethylbiphenyl-4,4'-dicarboxylic acid compounds can be used advantageously to produce high molecular weight film-forming or fiber forming polyesters and polycarbonamides. The polyesters of this invention comprises a polyhydroxy component comprising one or more polyhydric alcohols (diols, triols, etc.) and a polycarboxylic acid component comprising a 2,2',6,6'-tetramethylbiphenyl-4,4'-dicarboxylate component. The preferred polyesters of this invention are essentially linear and comprise units of alkylene glycols containing 2 to 12 carbon atoms and 2,2',6,6'-tetramethylbiphenyl-4,4'-dicarboxylate moieties. The polyesters based on 2,2',6,6'-tetramethylbiphenyl-4,4'-dicarboxylate have an exceptionally high Tg. For example, homopolymeric polyethylene 2,2',6,6'-tetramethylbiphenyl-4,4'-dicarboxylate has a Tg of about 191° C., homopolymeric tetramethylene 2,2',6,6'-tetramethylbiphenyl-4,4'-dicarboxylate has a Tg of 131° C., homopolymeric polyethylene terephthalate has a Tg of about 75° C. and homopolymeric polyethylene naphthalene 2,6-dicarboxylate has a Tg of 115°–125° C. Accordingly, the polyesters of this invention comprise 2,2',6,6'-tetramethylbiphenyl-4,4'-dicarboxylate moieties and polyhydric alcohol moieties.

Broadly speaking, the polyesters of this invention can be prepared by reacting the polyhydric alcohol or alcohols with the dicarboxylic acid component or components (acid or lower alkyl ester of dicarboxylic acid). An ester-forming derivative of the dicarboxylic acid may be used, i.e., an acid halide, a salt, its anhydride and/or an ester thereof, particularly an ester with a lower aliphatic alcohol or with phenol. Correspondingly, ester-forming derivatives of the polyhydric alcohols may be employed, i.e., a derivative of the alcohol containing functional groups equivalent to the hydroxyl groups in their ability to react with carboxyl groups. Thus, an alcohol may be employed in the form of an epoxide, and/or ester of the alcohol with acetic acid or other lower aliphatic acid may be used.

In a convenient method for preparing the dihydric alcohol dicarboxylate polyester, the dimethyl ester of the dicarboxylic acid or acids is reacted with an excess of the polyhydric alcohol, 1.1 to 2.5 moles of polyol per mole of ester, preferably employing about 1.5 to 2.1 moles of polyol per mole of ester. The reaction is usually carried out at atmospheric pressure but higher or lower pressure can be used if desired. A range is usually from 0.1 to ten atmospheres. Temperature is usually from 90° C. to 325° C. Following the ester interchange reaction, in which a lower alcohol is removed as a by-product, heating is continued at an increased temperature to bring about polycondensation. Small amounts of catalysts can be added to facilitate the reaction. Manganous acetate, calcium acetate, and sodium methoxide are typical ester interchange catalysts while antimony trioxide, dibutyltin maleate, and zinc acetate are suitable polycondensation catalysts. Litharge, sodium hydrogen hexabutoxytitanate and the tetra-alkyl titanates, such as tetra-isopropyl titanate, are examples of catalysts which may be used for both the ester interchange and the polycondensation steps. Normally, the polycondensation reaction is continued until a degree of polymerization is achieved corresponding to an inherent viscosity of approximately at least 0.2 dl/g in a 60/40 phenol-tetrachloroethane solvent at 30° C.

To achieve a higher degree of polymerization, the product of the polycondensation reaction is allowed to cool to room temperature, about 20° to 25° C., forming a solid material. The solid is ground to flake, following which the flake is heated below its melting point in a stream of inert gas to achieve solid phase condensation.

The tetramethylbiphenyldicarboxylic acid can provide from about 5 to 100 percent of the acyl equivalents in the polyester, preferably 20 to 100. Various other acid co-monomers include aromatic polycarboxylic acids, such as terephthalic acid, phthalic acid, phthalic anhydride, isophthalic acid, 2,6-naphthalene dicarboxylic acid, trimellitic anhydride, trimellitic acid, etc.; saturated aliphatic polycarboxylic acids, such as adipic acid, sebacic acid, 1, 2, 3, 4, butane-tetracarboxylic acid, etc.; unsaturated aliphatic dicarboxylic acids such as maleic acid, maleic anhydride, fumaric acid, etc. In general, the organic acids or acyl compounds containing three or more acyl groups comprise up to about 2% of the acyl equivalents in the polyester and the difunctional organic acids comprise at least 98%.

The polyhydric alcohols useful for producing the polyesters of this invention include alkylene glycols containing from about 2–12 carbon atoms, such as ethylene glycol, 1,2-propylene glycol, 1,3-propylene glycol, butylene glycol, hexamethylene glycol, dodecamethylene glycol, etc.; aromatic polyhydric alcohols, such as hydroquinone, resorcinol, Bisphenol A, etc.; cycloaliphatic glycols such as 1,4-dimethylol cyclohexane, dimethylol cyclobutane, etc.; polyoxyalkylene glycols, such as polyoxyethylene glycols, polyoxypropylene glycols, block copolymers of polyethylene and polypropylene glycol, polytetramethylene glycols, etc.; neopentyl glycol, polyhydric alcohols having three or more hydroxy groups, such as 1,1,1-trimethylol ethane, 1,1,1-trimethylol propane, penta arythritol, sorbitol, reaction products of the aforesaid polyhydric alcohols having a functionality of three or more with alkylene oxides (ethylene oxide and/or propylene oxide) such as those sold for use in the production of flexible polyurethane foams, etc. In general, the polyhydric alcohols having a functionality of three or more should provide no more than about 2 mole % of the polyester. For optimum fiber and film propeties, it is generally preferred that either ethylene glycol and/or butylene glycol comprise approximately 100 mole % of the polyol portion of the copolyester of this invention.

In those cases where an alpha, beta-ethylenically unsaturated acid compound (maleic anhydride, fumaric acid, etc.) is used, the resulting polyester can be dissolved in a monovinyl aromatic (styrene, vinyltoluene, etc.) and used in molding compositions in the same manner as other unsaturated polyesters.

The essentially linear polycarbonamides of this invention can be viewed as poly-2,2',6,6'-tetramethyl-4,4'-biphenyl dicarboxamides having arylene and/or alkylene groups joining the amido groups of the polymer. One or more of the alkylene or arylene groups can be joined by one or more heteroatoms

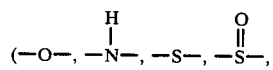

etc.) as is common in this art.

Suitable alkylene groups containing 2 to 24 carbon atoms include ethylene, trimethylene, hexamethylene, octamethylene, dodecamethylene,

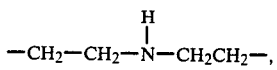

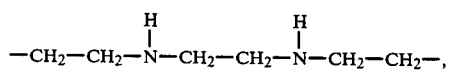

tetracosene, etc. Suitable arylene groups containing 6 to 24 carbon atoms include p-phenylene, o-phenylene, N,N-diphenyleneamine, oxydiphenylene, etc.

The high molecular weight polyamides can be prepared by well-known methods. These methods include reacting tetramethylbiphenyl dicarboxylic acid or its derivatives such as acid chlorides with alkylene and arylene diamines, diisocyanates, diisothiocyanates and their derivatives. For example, polyamides can be prepared from the free acid (2,2',6,6'-tetramethylbiphenyl-4,4'-dicarboxylic acid) and difunctional nitrogen containing compounds such as diphenylmethane-4,4'-diisocyanate, diphenylether-4,4'-diisocyanate, methylene bisaniline, p-phenylene diamine, etc.

In somewhat greater detail, the dicarboxylic acid can be reacted with an excess of the aromatic diamine, diisocyanate or diisothiocyanate. (1.1 to 2.5 moles of reactant per mole of acid, preferably about 1.5 to 2.1 moles of reactant per mole of acid). The reaction can be carried out at atmospheric pressure but higher or lower pressure can be used if desired. The temperature is usually from about 90° to 325° C. Small amounts of catalyst can be added to facilitate the reaction. Normally, the reaction is continued until the desired degree of polymerization is achieved.

EXAMPLE I

Fifteen grams cobaltous acetate was stirred into 200 ml acetic acid in a 500 ml three-necked round-bottom flask equipped with a thermometer, condenser, addition funnel, electric heating mantle and magnetic stirrer. Fifteen ml of 40% peracetic acid dissolved in acetic acid was added slowly to the flask from the dropping funnel. The color of the reactants changed from red (Co++) to green (Co+++). Five to ten minutes after the exothermic heat of reaction subsided, external heat was supplied to the mantle to maintain the reaction temperature at 45° C. After the dropping funnel was removed, ten grams bimesityl was added and a gas dispersion tube was inserted for the dropping funnel and oxygen was introduced at 0.3 SCFH. The reaction temperature was raised to 95° C. and held within a range of 90°–115° C. for five hours as indicated in Table I. Oxygen sparging and external heating were stopped and the reactants were allowed to cool to ambient temperature. The mixture was then filtered to obtain the precipitated solids, 2.7 grams and the filtrate was saved. The insolubles were washed three times with 5 ml. of acetic acid and then with concentrated hydrochloric acid to regenerate the free carboxylic acids. The regenerated acids were approximately 80% diacid and 20% monoacid.

The initial filtrate produced in the preceding paragraph was poured into one liter of water, the precipitate recovered, washed with more water, and then dissolved in 200 ml of ether. Extraction of the ether with 5% sodium bicarbonate (NaHCO$_3$) followed by acidification and filtration of the water extract yielded a fraction that was 85–90% biphenyl diacid. A similar extraction with 5% potassium hydroxide (KOH) gave a fraction that was 90–95% biphenyl mono-acid. The residue in all cases after ether evaporation was mainly unreacted bimesityl. The amounts of the various acids in these fractions were tabulated to give the results shown in the Table I. Table I lists pertinent data on four runs of selective bimesityl oxidation obtained by these methods.

TABLE I

Selective Oxidation of Pimesityl And Products Obtained

| | Reagents 10 Grams Bimesityl | | Temp | % Weight of Starting Materials | | | |
|---|---|---|---|---|---|---|---|
| Run | Co(OAc)$_2$—4H$_2$O | 40% CH$_3$COOOH | °C. | DA | MA | TA | Others |
| 1 | 10 | 10 | 90–104 | 29 | 45 | 1 | 4 |
| 2 | 10 | 10 | 100–105 | 25 | 48 | 1 | 3 |

TABLE I-continued

Selective Oxidation of Pimesityl And Products Obtained

| Run | Reagents 10 Grams Bimesityl | | Temp °C. | % Weight of Starting Materials | | | |
|---|---|---|---|---|---|---|---|
| | $Co(OAc)_2$—$4H_2O$ | 40% $CH_3COOOH$ | | DA | MA | TA | Others |
| 3 | 10 | 10 | 112–114 | 12 | 46 | 0.5 | 3 |
| 4 | 15 | 15 | 99–102 | 39 | 35 | 1 | 3 |

Notes:
DA - Diacid (2,2', 6,6'-tetramethylbiphenyl-4,4'-dicarboxylic acid)
MA - Monoacid (2,2', 4,6,6'-Pentamethylbiphenyl-4'-carboxylic acid)
TA - May be tri-acids
Others - Probably aldehydes and/or alcohols.

Analysis of these extracted fractions by nuclear magnetic resonance (NMR) was used to identify the major components present. Esterification gas chromatography (EGC) then indicated the quantitative percent of the major component together with the number and concentration of intermediates and by-products. The mass spectra of the esters from EGC also confirmed the identification of the major component and gave good evidence of the structure of the intermediates and by-products.

The crude diacid fraction (511 gms.) were mixed with 2.75 liters of methanol and 700 grams of dry hydrochloric acid in a 5 liter three-necked flask equipped with a thermometer, condenser, mechanical stirrer and separatory funnel and was heated at reflux (70°–73° C.) for 48 hours. The reaction mixture was cooled to room temperature and the precipitated solids were removed by filtration with a Buchner funnel. The precipitate was washed twice with methanol and dried. The methanol-soluble esters were recoverable by evaporating the methanol washings. The methanol-washed esters, 349 grams, were dissolved in 2.8 liters of ethyl ether. The solution was extracted five times in the separatory funnel, once with 60 ml of a 5% solution of sodium carbonate in water, once with 70 ml. of a 5% solution of sodium hydroxide in water and three times each with 100 ml of water. The solution was dried overnight over anhydrous calcium sulfate. The calcium sulfate was filtered out and the ethyl ether stripped off using atmospheric distillation. The residue was then vacuum flashed to a pot temperature of 270° C. at 9–11 mm of Hg. The flashed esters were then fractionally distilled in a ten-tray still to separate the diacid esters and the monoacid esters. The diacid esters were then recrystallized from benzene and vacuum dried. The dimethyl 2,2',6,6'-tetramethylbiphenyl-4,4'-dicarboxylate melted at 128°–129° C.

The diacid was recovered by heating the ester in KOH solution, acidifying with hydrochloric acid to excess hydrogen ion. The precipitated diacid was recovered by filtration. A water wash followed by drying under vacuum completed the purification of the 2,2',6,6'-tetramethylbiphenyl-4,4'-dicarboxylic acid.

EXAMPLE II

This example illustrates the production of high molecular weight polyamides and conversion into polyamide films suitable for high-temperature electrical insulation, typically having high dielectric constants.

One and one-half grams 2,2',6,6'-tetramethylbiphenyl-4,4'-dicarboxylic acid was dissolved in 5.8 grams of N-methyl-2-pyrrolidone in a small round-bottomed three-necked flask equipped with a thermometer, electric heating mantle and magnetic stirrer. The solution was heated to 150°–170° C. with stirring. Over a period of 45 minutes, 1.25 grams of diphenylmethane-4,4'-diisocyanate was added while maintaining the temperature at 150°–170° C. with stirring. Carbon dioxide was evolved. The temperature of 170° C. was maintained for an additional hour after which an additional 0.25 grams of diphenyl methane 4,4' diisocyanate were added. Heating and stirring were continued for another 30 minutes at 170° C. The solution was then diluted with 3.0 grams of N-methyl-pyrrolidone to reduce the viscosity to Z5-Z6 (Gardner-Holdt) at 20% solids. A second dilution with 3.0 grams of N-methylpyrrolidone was then made to reduce solids to 15%. A clear solution with viscosity of 40 Stokes resulted.

The inherent viscosity of the polyamide was determined using a Cannon-Fensky viscosimeter. The inherent viscosity was measured at 25° C. at a concentration of 0.5% by weight of the polymer in dimethyl acetamide.

A film was then cast from a 15% weight solution upon a glass plate and cured with heat. The Massachusetts Institute of Technology (MIT) film folding endurance test was used to measure film toughness.

EXAMPLE III

Example II was repeated using 1.5 grams 2,2',6,6'-tetramethylbiphenyl-4,4'-dicarboxylic acid and 1.75 grams diphenylether 4,4'-diisocyanate in place of the diphenylmethane diisocyanate (the same mole ratio of reactants). Solvent was added to adjust the resultant polymer solution to 15% weight solids with a viscosity greater than Z6 (Gardner-Holdt) and equal to 148 Stokes. Inherent viscosity was determined at 0.5% weight and cast film toughness determined.

EXAMPLE IV

This example illustrates the production of a polyamide from 2,2',6,6'-tetramethylbiphenyl-4,4'-diacyl chloride and a dimaine. The diacid chloride derivative was prepared by refluxing overnight 2.0 gms of the diacid in 20 ml of thionyl chloride with one drop of N,N-dimethylformamide as catalyst. Excess thionyl chloride was evaporated. The resulting crystalline residue was dried in a moderate vaccum at 50° C. for two days. The melting point was 197°–200° C.

The polyamide was prepared by reacting 2.2 gms of the diacid chloride derivative with 1.30 gms of methylene bisaniline in 15 gm of N,N-dimethyl acetamide (DMAC) as the solvent, at ambient temperature and pressure. The solvent mix was heated to 45°–50° C. for 45 minutes and then cooled to ambient temperature over a period of two hours. A clear viscous solution, viscosity 80 Stokes and 16% weight solids (calculated), resulted. DMAC was added to thin the polymer solution. Water was then added to precipitate the polymer which was separated by filtration. The crumbly granules of precipitated polymer were water-washed and dried overnight in a vacuum oven. The inherent viscosity at 0.5% weight concentration was determined. Cast film toughness was measured.

Product characterizations as to the films by the processes of Examples II to IV are summarized in Table II.

TABLE II

Polyamides From 2,2',6,6' Tetramethyl-4,4'-Dicarboxylic Acid

| Example | Inherent Viscosity[1] | Solution Viscosity[2] | Film Folding Endurance[3] |
|---|---|---|---|
| II | 0.90 | 40 | 6500-10,000 (1.2 Mils) |
| III | 1.08 | 150 | 300 (1.3 Mils) |
| IV | 0.86 | — | 15-50,000 (0.9 Mils) |

[1] 0.5% in DMAC (N,N—dimethyl acetamide)
[2] 15% solids in NMP (N—methyl-2-pyrrolidone)
[3] MIT Folding Endurance (Double Folds)

EXAMPLE V

This example illustrates the production of a high molecular weight homopolymeric polyethylene 2,2',6,6'-tetramethylbiphenyl-4,4'-dicarboxylate by ester interchange of the dimethyl ester with ethylene glycol in melt followed by solid state polymerization.

Five grams of dimethyl 2,2',6,6'-tetramethylbiphenyl-4,4'-dicarboxylate, 2.1 grams of ethylene glycol and 0.1 grams of dibutyltin maleate were heated at 180°-185° C. in a test tube equipped with a nitrogen bubbler and a side-arm. During the heating, nitrogen was slowly bubbled through the mixture. After the mixture was heated for two hours, the nitrogen flow was discontinued. A partial vacuum was pulled on the mixture over a period of 10 to 15 minutes, using a vacuum pump attached to the side-arm, and when the temperature rose to 260° C. a full vacuum (0.2 mm Hg) was applied and held for two hours. Inherent viscosity of the product was 0.21 deciliters per gram (dl/g), measured at a concentration of 0.4 grams per deciliter in a 60:40 by weight mixture of phenol and symmetrical tetrachloroethane.

The above product was ground to #10 mesh and heated in a test tube at 200°-210° C. and 0.05 mm Hg vacuum for 32 hours. After 16 hours, the white homopolymeric ethylene 2,2',6,6'-tetramethylbiphenyl-4,4'-dicarboxylate had an inherent viscosity of 0.59 dl/g. After the second 16 hours, the inherent viscosity was 0.84 dl/g.

EXAMPLE VI

This example illustrates melt polymerization to a relatively high I.V. One hundred twenty grams dimethyl 2,2',6,6'-tetramethylbiphenyl-4,4'-dicarboxylate, 45.6 grams of ethylene glycol, 0.1 grams of dibutyltin maleate, 0.05 grams of calcium acetate and 0.5 ml of antimony trisbutoxide were heated to 200° C. for two hours in a round bottom flask equipped with a mechanical stirrer and two side-arms. Nitrogen was bubbled slowly through the mixture during the period of heating with stirring. After two hours a partial vacuum was pulled on the mixture for 10 to 15 minutes, using a vacuum pump attached to the side-arm. When the temperature rose to 260° C., a full vacuum (0.1-2.2 mm Hg) was applied with continued stirring and kept for 8.0 hours. Inherent viscosity of the light brown homopolymer was 0.87 dl/g measured as described earlier. Strong fibers could be pulled from the melt.

Polymerization data with several diols are in Table III.

TABLE III

| | | | Polymerization Data | | | | |
|---|---|---|---|---|---|---|---|
| Diol | Diol Weight-Grams | M₂DMA Weight-Grams | Polymerization | Reaction Time Hrs/°C./mm Hg | Catalyst Amount | Melt I.V. (dl/g) | Polymer I.V. (dl/g) | Tg °C. |
| Ethylene Glycol | | | Solid State | 16/200-210°/0.1 | None (Control) | 0.18 | — | — |
| Ethylene Glycol | 2.1 | 5.0 | Melt | 2/260/0.2 | Sb/0.1 g | 0.30 | 0.27 | 184 |
| Ethylene Glycol | | | Solid State | 16/200-210°/0.1 | Sb* | | 0.64 | 191 |
| Ethylene Glycol | | | Solid State | 16/200-210/0.1 | Sn* | 0.21 | 0.59 | |
| Ethylene Glycol | | | Solid State | 32/200-210°/0.1 | Sn* | 0.21 | 0.84 | |
| 1,4-Butanediol | 2.7 | 4.5 | Melt | 2/260/0.2 | Ti/0.05 ml | | 0.37 | 131 |
| 1,6-Hexanediol | 3.6 | 4.5 | Melt | 2/260/0.2 | Ti/0.05 ml | | 0.31 | 97 |
| 1,10-Decanediol | 3.8 | 4.1 | Melt | 2/260/0.2 | Sb/0.05 g Sn/0.05 g | | 0.95 | 44 |

Sb - Antimony trisbutoxide
Sn - Dibutyl Tin Maleate
Ti - Tetra-n-butyl titanate
M₂DMe - Dimethyl tetramethylbiphenyldicarboxylate
*Additional catalyst not utilized

EXAMPLE VII

This example illustrates compression molding of a polyester film of this invention. Homopolymeric polyethylene 2,2',6,6'-tetramethylbiphenyl-4,4'-dicarboxylate having an I.V. of 0.87 dl/g was dried at 120° C. and 635 mm (30 inches) Hg overnight and placed between aluminum sheets and spacers to obtain the desired thickness. The polyester was placed in a press at 240° C. and held under pressure for five minutes. The sample was then removed from the press and allowed to cool without pressure. A fiberglass blanket was used to cover the sample in order to slow the cooling rate. Using this procedure, a 0.87 dl/g polyester powder was molded to give a film with a 0.77 dl/g inherent viscosity. The inherent viscosity loss was approximately the same as would be observed for poly(ethylene terephthalate). For compression molding of thicker parts up to 125 mils, a ten minute heating time was employed with a picture frame mold instead of aluminum sheets.

Physical properties of the film and shaped (molded) parts made according to the above procedure are given in the following table.

TABLE IV

| Properties of PEM$_2$ Film and Molded Parts | |
|---|---|
| Density, g/cm$^3$ | 1.12 |
| Glass Transition Temperature, °C. DTA | 191 |
| Rheovibron | 227 |
| Heat Deflection Temperature °C., 264 psi | 172 |
| Ultimate Tensile Strength, psi | 7658 |
| Elongation at Break, % | 4.1 |
| Flexural Modulus, psi | 282,000 |
| Young's Modulus dyne/cm$^2$ | 1 × 10$^{10}$ |
| Tensile Impact Strength, psi | 41 |
| Limiting Oxygen Index, % O$_2$ | 27–27.5 |

EXAMPLE VIII

This example illustrates the production of a polyester containing 2,2',6,6'-tetramethylbiphenyl-4,4'-dicarboxylate moieties, ethylene glycol moieties and polytetramethylene ether glycol moieties. Ten grams dimethyl 2,2',6,6'-tetramethylbiphenyl-4,4'-dicarboxylate (0.0307 moles). 4.2 grams ethylene glycol (0.0677 moles), 1.5 grams polytetramethylene ether glycol of molecular weight 560 (0.0023 moles) 0.1 gram dibutyltin maleate and 0.1 gram of calcium acetate were heated at 160° C. for 240 minutes in a test tube equipped with a nitrogen bubbler and a sidearm. During the heating, nitrogen was passed slowly through the mixture. A partial vacuum was pulled on the mixture over a period of 10 to 15 minutes, using a vacuum pump attached to the side-arm. After the temperature reached 275° C., full vacuum (0.9 mm Hg) was applied. The isolated polyester had a Tg of 120° C.

EXAMPLE IX

This example illustrates the production of polyester containing 2,2',6,6'-tetramethylbiphenyl-4,4'-dicarboxylate moieties, terephthalate moieties and ethylene glycol moieties. Three and one-tenth grams dimethyl terephthalate (0.016 mole), 1.3 grams (0.004 mole) dimethyl 2,2',6,6'-tetramethylbiphenyl-6,6'-dicarboxylate (M$_2$DMe), 2.8 grams (0.044 mole) ethylene glycol, 0.05 grams zinc acetate and 0.05 grams calcium acetate were heated at 160° C. for 120 minutes in a test tube equipped with a nitrogen bubbler and a side-arm. During the heating, nitrogen was passed slowly through the mixture. After two hours the temperature was raised to 210° C. and 0.05 ml antimony trisbutoxide was added. A partial vacuum was pulled on the mixture over a period of 10 to 15 minutes, using a vacuum pump attached to the side-arm. After the temperature was raised to 275° C., full vacuum (0.9 mm Hg) was applied and the reaction continued for 133 minutes. The copolyester containing a 4:1 mole ratio of terephthalate to tetramethylbiphenyl carboxylate moieties had an intrinsic viscosity of 0.29 deciliters per gram (dl/g), as determined in a 60/40 phenyl-tetrachloroethane mixed solvent at 30° C.

Copolyesters of ethylene terephthalate (ET) and ethylene 2,2',6,6'-tetramethylbiphenyl-6,6'-dicarboxylate (M$_2$D) in mole ratios 3:2, 2:3, and 1:4 were prepared in the same apparatus by the same procedure. The results are set forth below in Table IV.

TABLE IV

| Properties of the Copolyesters | | | | |
|---|---|---|---|---|
| Composition | Molar Ratio | I.V. dl/g | Tg °C. | Molding Temperature °C. |
| ET/M$_2$D | 1/0 | 0.60 | 74 | 275 |
| ET/M$_2$D | 4/1 | 0.29 | 95 | 140 |
| ET/M$_2$D | 3/2 | 0.31 | 119 | 140 |
| ET/M$_2$D | 2/3 | 0.55 | 145 | 185 |
| ET/M$_2$D | 1/4 | 0.40 | 169 | 210 |
| ET/M$_2$D | 0/1 | 0.64 | 191 | 240 |

The above data indicates that as the concentration of terephthalate moieties to tetramethylbiphenyl dicarboxylate moieties descreases, the molding temperature of the polymer increases. As the concentration of the tetramethylbiphenyl dicarboxylate moieties increases, the Tg of the polymer increases linearly. A 19:1 mole ratio terephthalate to tetramethylbiphenyl dicarboxylate polyester having an I.V. of 0.63 dl/g has a Tg of 78° C. and falls on the same line.

When the ethylene glycol in the 4:1 mole ratio terephthalate to tetramethylbiphenyl dicarboxylate polyester was replaced with tetramethylene glycol and the polyester was pepared in the same manner, a polyester was produced having an I.V. of 0.53 dl/g and a Tg of 52°–54° C. In this case also the Tg of the copolyester falls on linear line connecting the Tg points of homopolyesters of polytetramethylene terephthalate and polytetramethylene-2,2',6,6'-tetramethylbiphenyl-4,4'-dicarboxylate.

I claim:

1. A compound selected from the group consisting of 2,2',6,6'-tetramethylbiphenyl-4,4'-diacyl halide and diester of 2,2',6,6'-tetramethylbiphenyl-4,4'-dicarboxylic acid containing from 2 to 24 carbon atoms in each ester moiety.

2. The compound of claim 1, wherein said compound comprises 2,2',6,6'-tetramethylbiphenyl-4,4'-diacyl halide.

3. The compound of claim 2, wherein said diacyl halide comprises a diacyl chloride.

4. The compound of claim 1 wherein said compound comprises a diester containing 4 to 24 carbon atoms in each ester moiety.

5. The diester of claim 1 wherein said diester is a dialkyl ester and contains 4 to 13 carbon atoms per alkyl group.

6. The diester of claim 1 wherein the diester is the diethyl ester.

7. The diester of claim 1 wherein the diester is the diisopropyl ester.

* * * * *

UNITED STATES PATENT OFFICE
CERTIFICATE OF CORRECTION

Patent No. 4,582,925                    Dated April 15, 1986

Inventor(s)    John A. Donahue

It is certified that error appears in the above-identified patent and that said Letters Patent are hereby corrected as shown below:

Title Page "Division of Ser. No. 60,907" should be --Division of Ser. No. 60,909--.
U.S. Application Data "Continuation-in-part of Ser. No. 515,506" should be --continuation-in-part of Ser. No. 517,506--.
Column 1, line 5, "060,907" should be --60,909--.
Column 1, line 53 "consequently" should be --consequent--.
Column 2, line 2 "poymers" should be --polymers--.
Column 3, line 51 "comprises" should be --comprise--.
Column 6, line 61 "of Pimesityl" should be --of Bimesityl--.
Column 7, line 2 "of Pimesityl" should be --of Bimesityl--.
Column 8, line 59 "vaccum" should be --vacuum--.
Column 9, line 23 "Example V" --Heading should appear at Col. 9, line 43--.
Column 9, line 27 "$M_2DMA$" should be --$M_2DMe$--.

Signed and Sealed this

Second Day of September 1986

[SEAL]

Attest:

DONALD J. QUIGG

Attesting Officer      Commissioner of Patents and Trademarks